(12) United States Patent
Phillips et al.

(10) Patent No.: US 10,501,486 B2
(45) Date of Patent: Dec. 10, 2019

(54) STABILIZED ORGANOPHOSPHOROUS COMPOUNDS

(71) Applicant: Dow Technology Investments LLC, Midland, MI (US)

(72) Inventors: George R. Phillips, South Charleston, WV (US); Glenn A. Miller, South Charleston, WV (US); Marinus A. Bigi, Freeport, TX (US); Michael A. Brammer, Freeport, TX (US)

(73) Assignee: Dow Technology Investments LLC, Midlant, MI (US)

( * ) Notice: Subject to any disclaimer, the term of this patent is extended or adjusted under 35 U.S.C. 154(b) by 0 days.

(21) Appl. No.: 15/310,031

(22) PCT Filed: Apr. 20, 2015

(86) PCT No.: PCT/US2015/026648
§ 371 (c)(1),
(2) Date: Nov. 9, 2016

(87) PCT Pub. No.: WO2015/175158
PCT Pub. Date: Nov. 19, 2015

(65) Prior Publication Data
US 2017/0240578 A1    Aug. 24, 2017

Related U.S. Application Data

(60) Provisional application No. 61/993,118, filed on May 14, 2014.

(51) Int. Cl.
| C07C 45/50 | (2006.01) |
| C07C 47/02 | (2006.01) |
| B01J 31/18 | (2006.01) |
| C07D 233/56 | (2006.01) |
| C07F 9/6574 | (2006.01) |

(52) U.S. Cl.
CPC ......... *C07F 9/65746* (2013.01); *B01J 31/185* (2013.01); *C07C 45/50* (2013.01); *B01J 2231/321* (2013.01); *B01J 2531/822* (2013.01)

(58) Field of Classification Search
CPC .......... C07C 45/50; C07C 47/02; B01J 31/18; C07D 233/56
See application file for complete search history.

(56) References Cited

U.S. PATENT DOCUMENTS

| 3,283,037 A | 11/1966 | Davis |
| 3,415,906 A | 12/1968 | Shepard et al. |
| 3,437,720 A | 4/1969 | Guttag |
| 3,527,809 A | 9/1970 | Pruett et al. |
| 4,116,926 A | 9/1978 | York |
| 4,277,627 A | 7/1981 | Bryant et al. |
| 4,487,972 A | 12/1984 | Haag et al. |
| 4,567,302 A | 1/1986 | Sivaramakrishnan |
| 4,567,306 A | 1/1986 | Dennis et al. |
| 4,599,206 A | 7/1986 | Billig et al. |
| 4,650,894 A | 3/1987 | Fisch et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,059,710 A | 10/1991 | Abatjoglou et al. |
| 5,113,022 A | 5/1992 | Abatjoglou et al. |
| 5,179,055 A | 1/1993 | Wink et al. |
| 5,183,943 A | 2/1993 | Bryant et al. |
| 5,202,297 A | 4/1993 | Lorz et al. |
| 5,228,918 A | 7/1993 | Garand et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,312,996 A | 5/1994 | Packett |
| 5,325,113 A | 6/1994 | Takeda |
| 5,364,950 A | 11/1994 | Babin et al. |
| 5,391,801 A | 2/1995 | Sato et al. |
| 5,430,194 A | 7/1995 | Barner et al. |
| 5,449,653 A | 9/1995 | Briggs et al. |
| 5,527,950 A | 6/1996 | Hansen et al. |
| 5,681,473 A | 10/1997 | Miller et al. |
| 5,731,472 A | 3/1998 | Leung et al. |
| 5,741,942 A | 4/1998 | Bryant et al. |
| 5,741,944 A | 4/1998 | Bryant et al. |
| 5,744,649 A | 4/1998 | Bryant et al. |
| 5,744,650 A | 4/1998 | Nicholson et al. |
| 5,763,679 A | 6/1998 | Nicholson et al. |
| 7,223,374 B2 | 5/2007 | Magna et al. |
| 7,495,134 B2 | 2/2009 | Hess et al. |
| 8,461,394 B2 | 6/2013 | Lueken et al. |
| 9,174,907 B2 * | 11/2015 | Brammer ................. B01J 31/24 |
| 2006/0224000 A1 | 10/2006 | Papp et al. |
| 2013/0225849 A1 | 8/2013 | Berens et al. |

FOREIGN PATENT DOCUMENTS

| DE | 1800675 A1 | 4/1969 |
| DE | 102005042464 | 3/2007 |
| EP | 0149894 | 7/1985 |
| EP | 0285136 | 9/1985 |
| EP | 0577042 | 1/1994 |
| EP | 0590611 | 4/1994 |
| IN | 18833 | 9/2002 |

(Continued)

OTHER PUBLICATIONS

PCT/US2015/026648, International Search Report and Written Opinion dated Jul. 4, 2015.

(Continued)

*Primary Examiner* — Sun Jae Yoo

(57) ABSTRACT

A hydroformylation process wherein the hydrolyzable organophosphorous ligand component of the catalyst is supplied as a stabilized ligand composition comprising a hydrolyzable organophosphorous ligand and, per 100 moles compound, from 0.05 to 13 acid-neutralizing equivalents of an acid scavenger.

13 Claims, 1 Drawing Sheet

(56) References Cited

FOREIGN PATENT DOCUMENTS

| WO | 1997/020794 A1 | 6/1997 |
| WO | 1997/020798 | 6/1997 |
| WO | 2005/039762 | 5/2005 |
| WO | 2009/120210 | 10/2009 |
| WO | 2012/145241 | 10/2012 |
| WO | 2013/066712 | 5/2013 |
| WO | 2013/098370 | 7/2013 |
| WO | 2013/184350 | 12/2013 |
| WO | 2014/051975 | 4/2014 |
| WO | 2014149915 A1 | 9/2014 |

OTHER PUBLICATIONS

PCT/US2015/026648, International Preliminary Report on Patentability dated Nov. 24, 2016.
Fell, Journal Fuer Praktische Che, 1993, vol. 335, No. 1, p. 75-82.
Imaev, Journal of General Chemistry USSR, 1961, vol. 31, p. 1651-1653.

* cited by examiner

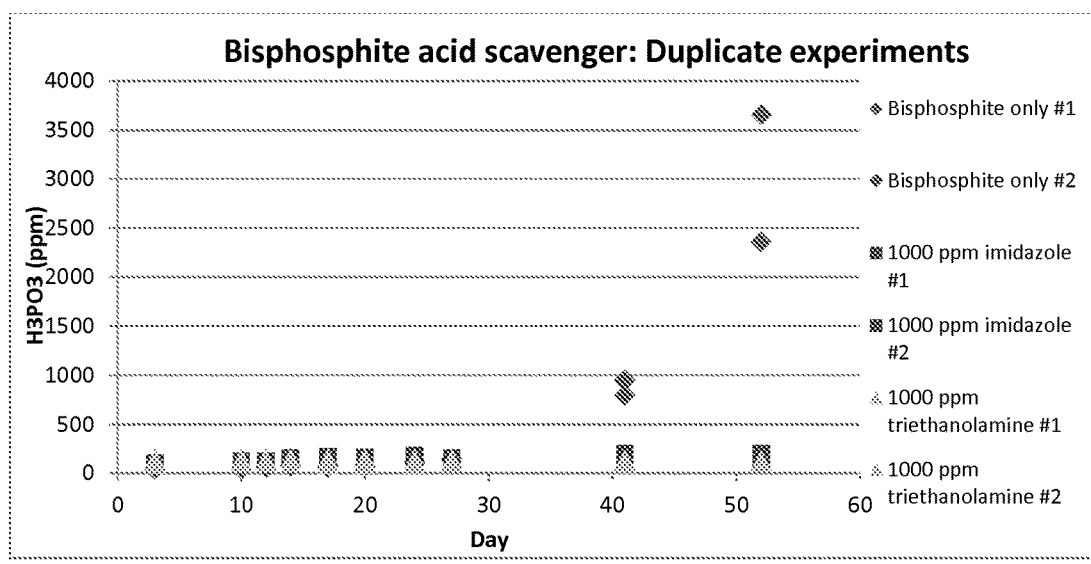

STABILIZED ORGANOPHOSPHOROUS COMPOUNDS

BACKGROUND OF THE INVENTION

The invention relates to a stabilized organophosphorous composition and a process for the preparation thereof.

Organophosphites and polyorganophosphites have been used for a variety of applications including preservatives (e.g., antioxidants) for plastic materials and as ligands for catalysts. However, maintaining the stability of phosphite ligands can be problematic. To be effective, the ligand and related catalyst must be stable under reaction conditions. The stability of the ligand can be negatively impacted by impurities, especially those that accumulate in the ligand during storage.

U.S. Pat. Nos. 3,283,037 and 3,437,720 discuss the stability of phosphites in air and at elevated temperature. U.S. Pat. No. 4,835,299 teaches how to remove impurities from organophosphites, but not how to prevent formation of the impurities.

WO 2013/066712 discusses the problem of residual solvent in polyorganophosphites and the impact of residual solvent on storage stability. In particular, residual solvent can contribute to ligand oxidation and/or hydrolysis. Similarly, WO 2013/098370 teaches that some solvates may result in clumping upon long term storage. US 2013/0225849 discloses the use of trace amounts of sodium methoxide as an additive in a washing step during the purification phase of the ligand manufacturing process to address the instability of polyorganophosphites in the presence of residual solvent. However, the presence of such an extremely strong base is not suitable in many catalytic processes, such as hydroformylation, hydrocyanation or hydrogenation. US 2013/0225849 also teaches that the strong base is removed prior to packaging. Thus, US 2013/0225849 teaches how to remove impurities from organophosphates, but not how to prevent formation of the impurities.

There is a need for a means to enhance the storage stability of hydrolyzable organophosphorus compounds that would not require compounds that are highly alkaline or otherwise not tolerated by downstream applications such as hydroformylation, hydrocyanation or hydrogenation.

SUMMARY OF THE INVENTION

The process of the invention comprises: (a) contacting CO, $H_2$, and at least one olefin in a reaction zone under hydroformylation conditions sufficient to form at least one aldehyde product in the presence of a catalyst comprising, as components, a transition metal and a hydrolyzable organophosphorous ligand, and (b) providing the ligand as a ligand composition comprising the ligand and from 0.05 to 13 acid-neutralizing equivalents of an acid scavenger per 100 moles ligand.

In another aspect, the invention includes a process for improving the storage stability of a ligand to be used as a catalyst component, the process comprising admixing a hydrolyzable organophosphorous ligand with from 0.05 to 13 equivalents of an acid scavenger per 100 moles of ligand to obtain a mixture of the ligand and the acid scavenger. The hydrolyzable organophosphorus ligand composition, i.e. the composition resulting from the admixing process, can be used to provide a ligand for use in the preparation of catalysts suitable for processes such as hydroformylation, hydrocyanation and hydrogenation.

Surprisingly, the addition of certain compounds to the hydrolyzable organophosphorous ligand prevents or minimizes the buildup of destabilizing impurities, such as phosphorous acids that can form when the ligand hydrolyzes, during storage without having a negative impact on the catalytic process(es) in which the ligand will be employed.

BRIEF DESCRIPTION OF THE DRAWINGS

FIG. 1 is a graph showing the results of Examples 1 and 2 and Comparative Experiment A.

DETAILED DESCRIPTION OF THE INVENTION

The process of the invention employs a hydrolyzable organophosphorous ligand and an acid scavenger.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

A hydrolyzable organophosphorous ligand is a trivalent phosphorous compound that contains at least one P—Z bond wherein Z is oxygen, nitrogen, chlorine, fluorine or bromine. Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligand may include chelate structures and/or may contain multiple P—Z moieties such as polyphosphites, polyphosphoramidites, etc. and mixed P—Z moieties such as phosphite-phosphoramidites, flurophosphite-phosphites, and the like. Examples of phosphite ligands include mono-organophosphite, diorganophosphite, triorganophosphite and organopolyphosphite compounds. Such organophosphorous compounds and methods for their preparation are well known in the art. Mixtures of hydrolyzable organophosphorous ligands can be employed.

Representative monoorganophosphites may include those having the formula:

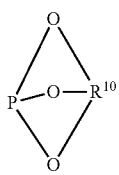
<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane and the like. Such monoorganophosphites may be found described in greater detail, for example, in U.S. Pat. No. 4,567,306.

Representative diorganophosphites may include those having the formula:

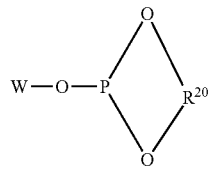
<<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302. Illustrative divalent aromatic radicals include, for example, arylene, bisarylene, arylene-alkylene, arylene-alkylene-arylene, arylene-oxy-arylene, arylene-$NR^{24}$-arylene wherein $R^{24}$ is as defined above, arylene-S-arylene, arylene-S-alkylene, and the like. More preferably $R^{20}$ is a divalent aromatic radical such as disclosed more fully in, for example, U.S. Pat. Nos. 4,599,206, 4,717,775, and 4,835,299.

Representative of a more preferred class of diorganophosphites are those of the formula:

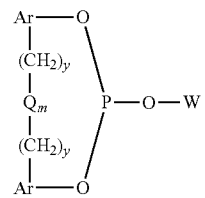
<<III>> wherein W is as defined above, each Ar is the same or different and represents a substituted or unsubstituted aryl radical, each y is the same or different and is a value of 0 or 1, Q represents a divalent bridging group selected from —$C(R^{33})_2$—, —O—, —S—, —$NR^{24}$—, $Si(R^{35})_2$ and —CO—, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

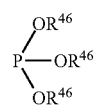
<<IV>> wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, dimethylphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3, 6-di-t-butyl-2-naphthyl)phosphite, bis(3,6,8-tri-t-butyl-2-naphthyl)phenylphosphite, bis(3,6,8-tri-t-butyl-2-naphthyl)(4-sulfonylphenyl)phosphite, and the like. The most preferred triorganophosphite is triphenylphosphite. Such triorganophosphites are described in greater detail, for example, in U.S. Pat. Nos. 3,527,809 and 5,277,532.

Representative organopolyphosphites contain two or more tertiary (trivalent) phosphorus atoms and may include those having the formula:

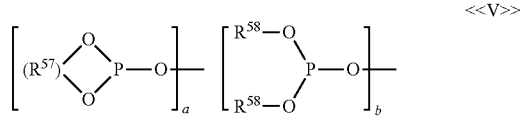

<<V>> wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each $R^{57}$ radical may be the same or different. Each $R^{58}$ radical may also be the same or different in any given compound.

Representative n-valent (preferably divalent) organic bridging radicals represented by X and representative divalent organic radicals represented by $R^{57}$ above, include both acyclic radicals and aromatic radicals, such as alkylene, alkylene-$Q_m$-alkylene, cycloalkylene, arylene, bisarylene, arylene-alkylene, arylene-$(CH_2)_y$-$Q_m$-$(CH_2)_y$-arylene radicals, and the like, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616; 5,364,950; and 5,527,950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

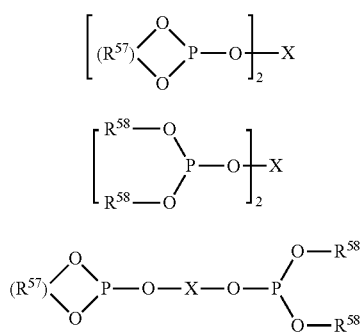

<<VI>>

<<VII>>

<<VIII>> wherein each $R^{57}$, $R^{58}$ and X of Formulas (VI) to (VIII) are the same as defined above for Formula (V). Preferably each $R^{57}$ and X represents a divalent hydrocarbon radical selected from alkylene, arylene, arylene-alkylene-arylene, and bisarylene, while each $R^{58}$ radical represents a monovalent hydrocarbon radical selected from alkyl and aryl radicals. Organophosphite compounds of such Formulas (V) to (VIII) may be found disclosed, for example, in U.S. Pat. Nos. 4,668,651; 4,748,261; 4,769,498; 4,774,361; 4,885, 401; 5,113,022; 5,179,055; 5,202,297; 5,235,113; 5,254, 741; 5,264,616; 5,312,996; 5,364,950; and 5,391,801.

$R^{10}$, $R^{20}$, $R^{46}$, $R^{57}$, $R^{58}$, Ar, Q, X, m, and y in Formulas (VI) to (VIII) are as defined above. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —C($R^{35}$)$_2$— where each $R^{35}$ is the same or different and represents hydrogen or a methyl radical. More preferably each alkyl radical of the above defined $R^8$ groups may contain from 1 to 24 carbon atoms and each aryl radical of the above-defined Ar, X, $R^{57}$ and $R^{58}$ groups of the above Formulas (VI) to (VII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, aralkyl, alkaryl and cyclohexyl substituents, may include for example silyl radicals such as —Si($R^{35}$)$_3$; amino radicals such as —N($R^{15}$)$_2$; phosphine radicals such as -aryl-P($R^{15}$)$_2$; acyl radicals such as —C(O)$R^{15}$ acyloxy radicals such as —OC(O)$R^{15}$; amido radicals such as —CON($R^{15}$)$_2$ and —N($R^{15}$)COR$^{15}$; sulfonyl radicals such as —SO$_2$R$^{15}$, alkoxy radicals such as —OR$^{15}$; sulfinyl radicals such as —SOR$^{15}$, phosphonyl radicals such as —P(O)($R^{15}$)$_2$, as well as halo, nitro, cyano, trifluoromethyl, hydroxy radicals, and the like, wherein each $R^{15}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —N($R^{15}$)$_2$ each $R^{15}$ taken together can also represent a divalent bridging group that forms a heterocyclic radical with the nitrogen atom, and in amido substituents such as —C(O)N($R^{15}$)$_2$ and —N($R^{15}$)COR$^5$ each $R^{15}$ bonded to N can also be hydrogen. It is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl, naphthyl, and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —$OCH_2CH_2OCH_3$, —$O(CH_2CH_2)_2OCH_3$, —$O(CH_2CH_2)_3OCH_3$, and the like; aryloxy radicals such as phenoxy and the like; as well as silyl radicals such as —$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; arylphosphine radicals such as —$P(C_6H_5)_2$ and the like; acyl radicals such as —$C(O)CH_3$, —$C(O)C_2H_5$, —$C(O)C_6H_5$, and the like; carbonyloxy radicals such as —$C(O)OCH_3$ and the like; oxycarbonyl radicals such as —$O(CO)C_6H_5$ and the like; amido radicals such as —$CONH_2$—$CON(CH_3)_2$, —$NHC(O)CH_3$, and the like; sulfonyl radicals such as —$S(O)_2 C_2H_5$ and the like; sulfinyl radicals such as —$S(O)CH_3$ and the like; sulfidyl radicals such as —$SCH_3$, —$SC_2H_5$, —$SC_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H_5)$, and the like.

Specific illustrative examples of such organophosphite compounds include the following: 2-t-butyl-4-methoxyphenyl(3,3'-di-t-butyl-5,5'-dimethoxy-1,1'-biphenyl-2,2'-diyl) phosphite, methyl(3,3'-di-t-butyl-5,5'-dimethoxy-1,1'-biphenyl-2,2'-diyl)phosphite, 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di[2,2'-(3,3',5,5'-tetrakis-tert-butyl-1,1-biphenyl)]-2,4-pentyldiphosphite, (2R,4R)di[2,2'-(3,3'-di-tert-butyl-5,5'-dimethoxy-1,1'-biphenyl)]-2,4-pentyldiphosphite, 2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis [2-(1,1-dimethylethyl)-4-methoxyphenyl]ester of phosphorous acid.

Hydrolyzable organophosphorous ligands and methods for their manufacture are well-known to those skilled in the art. In general, hydrolyzable organophosphorous ligands are produced by the reaction of $PCl_3$ with H—Z compounds, where Z is as defined herein, in the presence of a base (usually an amine or amine resin) then recrystallized (if a solid) before packaging. The actual synthetic route to the hydrolyzable organophosphorous ligand is not a critical feature of the invention nor does it mitigate the need to prevent degradation after production.

The acid scavenger is a compound that serves to increase the storage stability of the hydrolyzable organophosphorous ligand. Advantageously, the acid scavenger comprises at least one compound selected from the acid scavengers described hereinbelow. Mixtures of acid scavengers can be employed.

The scavenger is employed in an amount that will prevent or minimize the buildup during storage of destabilizing impurities, such as phosphorous acids that can form when the ligand hydrolyzes. The amount of the acid scavenger advantageously is sufficient to neutralize the amount of acid expected to form during storage. In one embodiment of the invention, the amount of acid scavenger is sufficient to provide from 0.05 to 13 acid-neutralizing equivalents per 100 moles ligand, preferably from 0.2 to 6 equivalents per 100 moles ligand, and most preferably from 0.5 to 2 equivalents per 100 moles ligand. The upper limit on the amount of acid scavenger is primarily determined by economics. Generally speaking, there is little benefit above about 13 equivalents acid scavenger per 100 moles ligand. The amount of acid scavenger is based on the hydrolyzable organophosphorous ligand as packaged and stored and before use in a downstream process, e.g., a hydroformylation process. In one embodiment of the invention, the amount of scavenger employed is based on the observation of the decomposition rate of the ligand composition being stored, and/or on historical observation of prior batches.

For the purposes of the invention, the term "acid-neutralizing equivalent" refers to the number of equivalents of acid scavenger needed to convert an acid to its salt. Thus, strong acids formed by the hydrolysis of the ligand to generate phosphorous-containing acids, such as phosphoric acid, phosphorous acid, and the like, react with the acid scavenger to form a neutralized salt that has a much lower acid strength. The resulting neutralized salt has a higher pKa than the original acid. Each acid moiety reacts with one neutralizing agent moiety. Since the acids may be capable of generating more than one acid moiety, and the scavengers may be capable of neutralizing more than one acid moiety, it is recognized by those skilled in the art that multiple neutralizations may occur per mole of ligand. For example, a bisphosphite (with two phosphorous atoms) may degrade to liberate two moles of bifunctional phosphorous acid, and thus requires 4 equivalents of acid neutralization. Likewise, some acid neutralizing agents such as, for example, bis(2, 2,6,6-tetramethyl-4-piperidyl) sebacate may neutralize more than one acid moiety per mole. The resulting neutralized salt advantageously has a pKa of from 5 to 10.

Depending on the level of acid scavenger employed, the molecular weight of the acid scavenger, and the amounts of other components in the hydrolyzable organophosphorous ligand composition, e.g., residual solvents, impurities, inert materials and other additives such as anti-caking additives, the combined amount of the ligand and acid-scavenger, not counting the above other components, can be at least 50 wt %, preferably 90 wt %, more preferably at least 95 wt %, and even more preferably at least 98 wt %, based on the total weight of the ligand composition.

Examples of one type of acid scavenger include those with the structure:

(IX)

wherein $R^{32}$, $R^{33}$, and $R^{34}$ represent H, alkyl or aryl substituents, provided that no more than one of $R^{32}$, $R^{33}$, and $R^{34}$ can be hydrogen, while preferably none are hydrogen, and preferably at least 1 is an electron withdrawing substituent, most preferably 2 are electron withdrawing substituents. The electron withdrawing alkyl or aryl substituents include alkyl-substituted or unsubstituted aryl, halogenated, alkoxylated, alkylalkoxylated, or carboxylated aryl groups, beta-alkoxy or beta-alkoxyalkyls (such as beta-hydroxyethyl, beta-hydroxy-alpha-methylethyl, beta-hydroxy-betamethylethyl and ethoxylated and/or propoxylated adducts thereof), Preferred acid scavengers of the preceding formula include triethanolamine, methyldiethanolamine, dimethylethanolamine, ethyldiethanolamine and tri-propoxylamine.

One class of acid scavenger is shown in formula (X):

wherein each $R^{36}$ independently is selected from $C_1$-$C_4$ alkyl, hydroxyl (and ethoxylated and/or propoxylated adducts thereof), alkylalkoxy, or halogen, x is 1-3 and z is 0-6. Preferably, multiple $R^{36}$ moieties are present, and may be the same or different, and, most preferably, at least one such moiety is located on each side of the nitrogen moiety. Preferred acid scavengers of the preceding formula include 4-hydroxyl-2,2,6,6-tetramethylpiperidine and its derivatives, such as bis(2,2,6,6-tetramethyl-4-piperidyl) sebacate.

Another family or class of acid scavenger is the pyridines and related cyclic structures of the following formula:

wherein $R^{36}$ is as described above and q is 0-5. Preferably, at least one $R^{36}$ is not H, and more preferably the non-H substituent is in the ortho position. Even more preferably, non-H substituents are in both ortho-positions.

Additional examples of suitable acid scavengers include weakly basic amines such as imidazoles, pyrazoles, indazoles, 1,2,3-triazoles, 1,2,4-triazoles, 2,1,3-triazoles, 4,1,2-triazoles, 1,2-diazines, 1,3-diazines, 1,4-diazines, 1,3,5-triazines, and benzimidazoles preferably with substituents such as described for $R^{32}$ that increase the water solubility of the weakly basic amine. Oxyacid salts such as sodium or potassium phosphates, citrates, maleates, fumarates, and the like can also be used as acid scavengers.

In one embodiment of the invention, when the hydrolyzable organophosphorous ligand is polar, such as in the case of ionic phosphites, e.g., those described in U.S. Pat. No. 5,059,710, acid scavengers with very low water solubility are advantageously employed, such that excess acid scavenger is removed in the non-polar product phase during a phase separation process.

The ligand composition of the invention advantageously is prepared by admixing the acid scavenger with the hydrolyzable organophosphorous ligand. The admixing can be conducted during or, depending on the manufacturing process, after manufacture of the hydrolyzable organophosphorous ligand. The admixing can be achieved according to methods, and using equipment, well known to those skilled in the art. In various embodiments of the invention, the ligand composition comprises, consists essentially of, or consists of, a hydrolyzable organophosphorous ligand and, per 100 moles ligand, from 0.05 to 13 equivalents of the acid scavenger, preferably from 0.2 to 6 equivalents, and most preferably from 0.5 to 2 equivalents.

The acid scavenger is preferably added during the final recrystallization step of the ligand manufacturing process, or is admixed with solid hydrolyzable organophosphorous ligand before or during packaging. For example, in the final recrystallization, adding a solution containing the acid scavenger as part of the recrystallization solvent will deposit some of the acid scavenger when the residual mother liquour is evaporated during the drying step. Alternatively, a double-cone solids mixer or similar device can be employed to disperse the acid scavenger in solid hydrolyzable organophosphorous ligand prior to final packaging. Other well known methods of introducing the acid scavenger can be employed. Advantageously, the acid scavenger is well distributed in the hydrolyzable organophosphorous ligand. Preferably, the acid scavenger forms a substantially homogeneous mixture with the hydrolyzable organophosphorous ligand. In the case of a ligand that is a liquid under ambient conditions, introducing the acid scavenger into the ligand in the liquid phase can done simply by dissolving the acid scavenger directly into the ligand. For all ligands, the acid scavenger may be added to a ligand solution followed by removal of the solvent, if desired. Removal of the solvent is preferred.

Packaging of the admixed material is advantageously performed according to methods known to those skilled in the art. The ligand composition advantageously is stored in a container under an inert atmosphere, preferably with low humidity such as, for example, less than 70% relative humidity, less than 60% relative humidity, or less than 50% relative humidity, with lower humidities being more preferred. By "inert atmosphere" it is meant that the atmosphere is substantially free of the following: oxidizers such as, for example, $O_2$, ozone, or peroxides such as $H_2O_2$; acids, e.g., HCl; sulfur-containing species; and the like. Preferred gases of the storage atmosphere are non-flammable. Examples of suitable gases include $N_2$, Ar, He, $CO_2$, and the like, with $N_2$ being most preferred. Advantageously, the admixed material is stored in appropriate air-tight storage containers such as, e.g., steel drums, glass containers, or oxygen impermeable plastic containers. The rate of ligand decomposition is presumed to be related to the exposure of the P(III) moiety to oxygen and moisture. Accordingly well-known measures to avoid exposure to an adverse atmosphere are advantageously employed during storage of the ligand composition. In one embodiment of the invention, the ligand composition is stored in the substantial absence of a liquid. In various embodiments of the invention, the ligand composition is stored for a period of at least 30 days, at least 60 days, at least 90 days, at least 180 days, at least 360 days or at least 720 days.

The progress of decomposition or degradation can readily be measured by taking samples of the packaged material and analyzing for degradation by conventional means. For example, samples can be analyzed by extraction of the ligand with water, and then measuring the acidity of the water extract by conventional methods, such as acid/base titration or pH determination methods, e.g., using a pH meter or using pH indicating paper. Ion chromatography or high pressure liquid chromatography (HPLC) can also be used to measure acidic species in the compound or a water extract. Samples analyzed over time generate a rate of degradation that may exhibit an "autocatalytic" profile. The success of an acid scavenger can be judged by the reduction of the rate of increase of acidic species with time.

The ligand composition can be used in a wide range of applications where hydrolyzable organophosphorous ligands are employed. The composition is especially useful for applications in which a hydrolyzable organophosphorous ligand is to be stored for extended periods of time. For example, a ligand composition can be employed in a hydroformylation, hydrocyanation, and/or hydrogenation process. The hydroformylation process, and conditions for its operation, are well known. A hydroformylation process may be conducted in any batch, continuous or semi-continuous fashion and may involve any catalyst liquid and/or gas recycle operation desired.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

Illustrative metal-organophosphorous ligand complexes employable in such hydroformylation, hydrocyanation, and/or hydrogenation reactions include metal-organophosphorous ligand complex catalysts. These catalysts, as well as methods for their preparation, are well known in the art and include those disclosed in the patents mentioned herein. In general, such catalysts may be preformed or formed in situ and comprise metal in complex combination with an organophosphorous ligand, carbon monoxide and optionally hydrogen. The ligand complex species may be present in mononuclear, dinuclear and/or higher nuclearity forms. However, the exact structure of the catalyst is not known.

The reaction conditions of the hydroformylation processes may include any suitable type hydroformylation conditions heretofore employed for producing optically active and/or non-optically active aldehydes. For instance, the total gas pressure of hydrogen, carbon monoxide and olefin starting compound of the hydroformylation process may range from 1 to 69,000 kPa. In general, the molar ratio of gaseous $H_2$:CO may range from 1:10 to 100:1 or higher, the more preferred molar ratio being from 1:10 to 10:1. Advantageously, the hydroformylation process is conducted at a reaction temperature from −25° C. to 200° C., preferably from 50° C. to 120° C.

The recycle procedure, when employed, generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. Nos. 5,430,194 and 5,681,473, or by the more conventional and preferred method of distilling it, i.e., vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled to the hydroformylation zone (reactor) in any conventional manner desired.

The ligand composition, and optionally the catalytic metal, are charged to the hydroformylation system via a catalyst mix tank or similar system where they are dissolved in solvent and introduced to the reaction zone. In some cases, the catalyst mix tank and the reaction zone can be the same. The ligand composition also may be introduced to the hydroformylation system at one or more other points such as, for example, the aqueous treatment zone and/or the vaporizer, in addition to or instead of charging the ligand composition to the reaction zone.

In the above described recycle process, the use of an aqueous (preferably buffered) solution, such as in an extraction system, to prevent and/or lessen hydrolytic degradation of the organophosphite ligand and deactivation of a metal-organophosphite ligand complex is disclosed in U.S. Pat. Nos. 5,741,942 and 5,741,944. The aqueous treatment zone (extraction zone, e.g., an extractor) can be used to remove neutralized acid-salts formed during storage and excess acid scavenger. In one embodiment of the invention, the extraction system will remove these degradation products as well as the neutralized acid-salts and unused acid scavenger, thereby preventing their buildup in the system, which may contribute to aldehyde heavies formation, precipitation in process fluids, or other undesirable effects. This route of removal is preferable over being removed with the product (e.g., vaporized). Based on this, preference is given to water soluble, high boiling acid scavengers to enhance water partitioning and removal by the aqueous extraction system. Filtration or centrifugation can also be used to remove insoluble neutralized salts as well. In one embodiment of the invention, an aldehyde-containing stream is taken from the reaction zone and is at least partially forwarded to an extraction zone, wherein the acid scavenger is substantially removed from the aldehyde.

SPECIFIC EMBODIMENTS OF THE INVENTION

All parts and percentages in the following examples are by weight unless otherwise indicated. Pressures are given as absolute pressure unless otherwise indicated. All manipulations are done in a $N_2$-glove box to exclude air and moisture unless otherwise indicated.

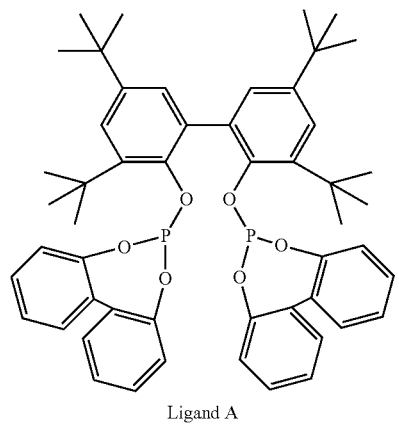 [SMILES: CC(C)(C)c1cc(-c2cc(C(C)(C)C)cc(C(C)(C)C)c2Op2oc3ccccc3c3ccccc3o2)c(Op2oc3ccccc3c3ccccc3o2)c(C(C)(C)C)c1]

Ligand A

EXAMPLES 1 AND 2

Samples of Ligand A are prepared as described in WO 2009/120210. Then, as an acid scavenger, either triethanolamine (Ex. 1; Aldrich, 5.0 mg) or imidazole (Ex. 2; Aldrich, 5.0 mg) and solid Ligand A (5.0 g, containing <100 ppmw phosphorous acid, $H_3PO_3$) are sequentially weighed into a round wide-mouth polyethylene jar (approx. 4 inches deep and 3 inches wide). This corresponds to 0.6 and 1.2 acid neutralizing equivalents of acid scavenger per 100 moles of Ligand A for triethanolamine and imidazole, respectively.

Each experiment is performed in duplicate. Each sample is then removed from the $N_2$-glove box one at a time and 25 mL of near-boiling ethyl acetate (Aldrich, 60° C.) is quickly poured into the sample jars and the resulting suspension (the bisphosphite ligand did not fully dissolve) is stirred thoroughly, while any large solids are crushed with a metal spatula. A vigorous stream of nitrogen is then directed over the suspension for 30 minutes to remove the ethyl acetate and the resulting white cake is crushed into a powder with a metal spatula. This procedure models the deposition of the acid scavenger in the ligand during the final recrystallization.

After all the samples are processed, they are left uncovered and exposed to ambient laboratory atmosphere in a fume hood as an accelerated aging test. Samples are removed periodically from each jar over a period of several months and are tested for phosphite concentration using ion chromatography. The results are shown in FIG. 1.

COMPARATIVE EXPERIMENT A

The procedure of Example 1 is repeated except that no acid scavenger is added to the ligand. The results are shown in FIG. 1.

The starting phosphorus acid level of the Ligand A is approximately 100 ppm, and the data shows that the phosphorus acid levels do not substantially increase after the acid scavengers are added. The control (Comparative Experiment A) clearly shows the autocatalytic decomposition of the ligand while the samples with the acid scavenger exhibit negligible change in the rate of degradation.

EXAMPLE 3 AND CONTROL EXPERIMENT

Following the accelerated aging test, samples of the stabilized materials of Examples 1 and 2 are employed in a rhodium-catalyzed propylene hydroformylation reaction to observe activity and product isomer ratio. This activity testing is performed by using the stabilized materials in the conventional hydroformylation process of U.S. Pat. No. 4,277,627 (Examples 1-33) using the conditions given below, and gas chromatography is used to determine the isomer ratio. No stabilizer is used in the Control Experiment, which is not an embodiment of the invention.

TABLE 1

| Run | Acid scavenger | Activity | Isomer ratio (n-butanal/ isobutanal) |
|---|---|---|---|
| Control | Fresh Ligand (unaged, no acid scavenger) | 1.8 mol/L · hr | 27:1 |
| Ligand Comp'n of Ex. 2 | Imidazole | 2.0 mol/L · hr | 26:1 |
| Ligand Comp'n of Ex. 1 | Triethanolamine | 1.9 mol/L · hr | 26:1 |

(2:1 L:Rh and 50 ppm Rh with 1:1:1 $CO:H_2$:propylene

The results, shown in Table 1, demonstrate that these levels of acid scavenger (roughly 1 equivalent per 100 moles ligand, or about 1000 ppmw) do not impact hydroformylation activity or isomer ratio compared to fresh ligand, within experimental error.

These experiments demonstrate that the addition of the acid scavenger to the hydrolyzable organophosphorous ligand surprisingly minimizes degradation of the ligand during storage while not having a negative impact on the catalytic process for which the stabilized hydrolyzable organophosphorous ligand is employed. It is expected that the same degree of success will be observed when larger quantities of ligand, such as drum quantities, isotainer quantities, and the like, are employed.

What is claimed is:

1. A process comprising: (a) contacting CO, $H_2$, and at least one olefin in a reaction zone of a hydroformylation system under hydroformylation conditions sufficient to form at least one aldehyde product in the presence of a catalyst comprising, as components, a transition metal and a hydrolyzable organophosphorous ligand, (b) providing the ligand as a ligand composition comprising the ligand and from 0.05 to 13 acid-neutralizing equivalents of an acid scavenger per 100 moles ligand, and (c) prior to providing the ligand composition, storing the ligand composition under a substantially oxidizer-free atmosphere, under vacuum, or both.

2. The process of claim 1 wherein the ligand composition is stored for a period of at least 30 days.

3. The process of claim 1 wherein the acid scavenger includes at least one compound selected from: triethanolamine (TEA) and ethoxylates thereof, methyldiethoxyamine, dimethylethoxyamine, ethyldiethoxyamine, tri-3-propoxyamine, tri-(2-(methanol)ethyl)amine, tri-isopropanolamine and propoxylates thereof, 4-hydroxyl-2,2,6, 6-tetramethylpiperidine, bis(2,2,6,6-tetramethyl-4-piperidyl) sebacate, triethylamine, tri-n-propylamine, tri-n-butylamine, tri-iso-butylamine, tri-iso-propylamine, tri-n-hexylamine, tri-n-octylamine, dimethyl-iso-propylamine, dimethyl-hexadecylamine, methyl-di-n-octylamine, N,N-dimethylaniline, N,N-diethylaniline, N,N-dimethyl-p-toluidine, N-methyldiphenylamine, N,N-dimethylbenzylamine, N,N-dimethyl-1-naphthylamine, N,N, N',N'-tetramethylethylene diamine, 1,4-diazabicyclo-[2,2,2]-octane, pyridine, picoline, lutidine, collidine, N-methylpiperidine, N-methylmorpholine, N-2'-hydroxyethylmorpholine, quinoline, isoquinoline, quinoxaline, acridien, quinuclidine, imidazole, benzimidazole and benztriazole, sodium and/or potassium salts of phosphoric acid, sodium and/or potassium salts of citric acid, sodium and/or potassium salts of maleic acid, and sodium and/or potassium salts of fumaric acid.

4. The process of claim 1 wherein the acid scavenger includes at least one compound selected from triethanolamine, methyldiethanolamine, dimethylethanolamine, ethyldiethanolamine, tri-3-propoxyamine, tri-(2-(methanol) ethyl)amine, tri-isopropanolamine, triethylamine, pyridine, N,N-dimethylaniline, 4-hydroxyl-2,2,6,6-tetramethylpiperidine, bis(2,2,6,6-tetramethyl-4-piperidyl) sebacate, imidazole, benzimidazole, trisodium phosphate, and di-sodium maleate.

5. The process of claim 1 wherein the acid scavenger includes TEA.

6. The process of claim 1 wherein the acid scavenger is TEA.

7. The process of claim 1 wherein the amount of acid scavenger is from 0.2 to 6 equivalents of the acid scavenger per 100 moles ligand.

8. The process of claim 1 wherein the amount of acid scavenger is from 0.5 to 2 equivalents of the acid scavenger per 100 moles ligand.

9. The process of claim 1 wherein the hydrolyzable organophosphorous ligand is primarily in the solid phase.

10. The process of claim 1 wherein the hydrolyzable organophosphorous ligand is primarily in the liquid phase.

11. The process of claim 1 wherein the composition consists essentially of a hydrolyzable organophosphorous ligand and, per 100 moles compound, from 0.05 to 13 equivalents of the acid scavenger.

12. The process of claim 1 wherein an aldehyde-containing stream is taken from the reaction zone and is at least partly forwarded to an extraction zone, and wherein in the extraction zone the acid scavenger is substantially removed from the aldehyde.

13. A process for improving the storage stability of a ligand to be used as a catalyst component, the process comprising admixing a hydrolyzable organophosphorous ligand with from 0.05 to 13 equivalents of an acid scavenger per 100 moles of ligand to obtain a mixture of the ligand and the acid scavenger.

* * * * *